United States Patent [19]

Allen et al.

[11] Patent Number: 4,924,502
[45] Date of Patent: May 8, 1990

[54] MEANS FOR STABILIZING SOUND PRESSURE PRODUCED AT THE EARDRUM UNDER AN EARPAD

[76] Inventors: Clayton H. Allen, 80 South Rd., Chebeague Island, Me. 04017-9710; Elliott H. Berger, 7911 Zionsville Rd., Indianapolis, Ind. 46268-0898

[21] Appl. No.: 47,790

[22] Filed: May 8, 1987

[51] Int. Cl.$^5$ .......................... H04R 1/10; H04R 1/28
[52] U.S. Cl. ........................................ 381/72; 381/71; 381/94; 381/158; 381/187; 181/129
[58] Field of Search ....................... 381/71, 72, 153, 94, 381/154, 183, 158, 187; 2/209; 181/129, 135

[56] References Cited

U.S. PATENT DOCUMENTS

| | | | |
|---|---|---|---|
| 2,529,562 | 11/1940 | Martin | 381/187 |
| 3,160,717 | 12/1964 | Beguin | 381/167 |
| 3,621,488 | 11/1971 | Gales | 181/129 |
| 3,862,379 | 1/1975 | Pless | 381/187 |
| 4,071,717 | 1/1978 | Fidi et al. | 181/129 |
| 4,160,135 | 7/1979 | Görike | 381/187 |
| 4,239,945 | 12/1980 | Atoji et al. | 381/187 |
| 4,418,248 | 11/1983 | Mathis | 381/183 |
| 4,441,576 | 4/1984 | Allen | 181/129 |

Primary Examiner—Jin F. Ng
Assistant Examiner—Danita R. Byrd
Attorney, Agent, or Firm—Fish & Richardson

[57] ABSTRACT

In a hearing device, such as a circumaural earmuff cup or a circumaural earphone cup, either of which comprises an earpad assembly in contact with the external ear, through which sound is conducted to the external ear for the purpose of providing at the eardrum a sound pressure having a prescribed ratio with respect to the sound pressure at a source, the invention comprising a predetermined sound leakage path through said earpad assembly, to reduce the variable in said ratio, that is customarily encountered caused by the variations in the shape of the external ear from one user to another and by variations in position and force of contact of the earpad resting against the pinna.

11 Claims, 6 Drawing Sheets

SECTION A-A

SECTION B-B

SECTION A-A

SECTION B-B

SECTION A-A

SECTION B-B

SECTION C-C

MEANS FOR STABILIZING SOUND PRESSURE PRODUCED AT THE EARDRUM UNDER AN EARPAD

This invention relates to the field of hearing protection, hearing threshold evaluation and the production of high quality sound reproduction at the ear.

Hearing protection devices serve to prevent a loss of hearing resulting from extended exposures to loud noise, such as encountered, for example, in many industrial working environments and in some forms of military service and recreational activities.

As described in greater detail in U.S. Pat. No. 4,441,576 issued, Apr. 11, 1984 to C. H. Allen, in some applications, where sound levels vary over a wide range, it is advantageous to utilize a nonlinear passive acoustic filter as a bypass element in combination with a conventional hearing protection device (HPD) to provide a reduced sound attenuation during intervals of low sound levels in order to maximize the recognition of speech and other sounds important to safety and effective functioning of the user in the noisy environment and to provide an automatic, instantaneous increase in sound attenuation during any interval of high sound level, such as encountered from gun fire, forging hammers and the like at close range.

While it is beneficial to reduce the noise attenuation during quieter intervals, there is often sufficient background noise to require some moderate amount of noise attenuation to assure a sufficient hearing protection during these intervals. Therefore, it is important to have both a reliable minimum, and an adequate amount of noise reduction for the intended application.

When the nonlinear bypass element was used to admit sound through the shell of a circumaural earcup, it was observed that the large volume of the cavity, enclosed by the earcup, acted as a "short circuit" for the sound entering through the bypass element, particularly at high frequencies. This prevented the presentation at the ear of an attenuated sound signal that faithfully represented the external signals over the frequency range of interest. In order to attain the reduced attenuation over a broad frequency range, when the nonlinear acoustic filter is used as a bypass element to carry sound through the shell of a circumaural earcup, it was found essential to define an acoustical path of small volume that utilized an earpad assembly comprising an acoustical duct to carry sound from the nonlinear bypass element directly to the eardrum through an earpad cushion pressed lightly into contact against the pinna of the ear. Large variations in level and spectral shape of the insertion loss at the ear were then found to be caused by naturally occurring uncontrolled acoustical leaks between the surface of the earpad cushion and the surfaces of the external ear, due to the irregular shape of the pinna and variations in the positioning and force of contact of the earpad cushion against the pinna.

Changes in excess of 20 dB were occasionally observed at some frequencies when large naturally occurring, acoustical leaks were sealed by the use of a soft, conformable material such as modeling clay, or the like, between the earpad and the pinna. Such large variations are, of course, intolerable when attempting to provide both a minimum and a reliably safe insertion loss for all users.

SUMMARY OF THE INVENTION

It has been found that such variations can be greatly reduced by providing a controlled acoustical leakage path, having a prescribed acoustic impedance, through the earpad assembly to assure at least a minimum amount of sound passage into the larger acoustical cavity outside of the duct but inside the space enclosed by the shell and the cushion of the earcup assembly. With a properly sized, controlled leakage path and with the addition of suitable sound absorptive material in that leakage path, the variations in insertion loss level have been controlled generally within ±4 dB or less over a wide frequency range.

This same use of a prescribed leakage path through an earpad assembly is applicable to the reduction of variations in sound level at the ear for other devices such as earphones, headsets and the like, where sound levels generated by an electroacoustic transducer are used to reproduce sounds of high fidelity at the ear while using a circumaural earcup enclosure for excluding the surrounding ambient noise, whether or not used in conjunction with a prescribed nonlinear passive acoustic filter, such as herebefore described, as one sound source.

A similar use of a leakage path is applicable where an electroacoustic transducer is used to measure the hearing threshold of a person, as in the audiometric tests administered as part of a hearing conservation program. Such tests require the generation of a consistent and known sound level at the eardrum for all subjects tested, in order to obtain reliable results.

Accordingly, it is an important object of this invention to provide a means of stabilizing the sound pressure produced at the eardrum under an earpad assembly through which sound passes from a sound source, thereby minimizing the variation in sound pressure at the eardrum resulting from variations in the leakage path naturally occurring between the earpad cushion and the pinna due to variations in positioning and force of contact between the earpad and the pinna of the ear or due to variations in the size and shape of the pinna from one person to another.

It is a further object to provide means for reducing or eliminating the effect of acoustic resonances between the major cavity of the ear cup assembly and the smaller cavity comprising the principal acoustic path from the source to the eardrum.

It is a further object to provide means that aid in adjusting the spectral shape of the insertion loss spectrum of the principal acoustic path between a sound source and the eardrum, at least over a portion of the audible frequency range from 100 to 10,000 Hz.

It is a further object to provide means for minimizing the deviation of the sound level at the eardrum of a subject with respect to a standardized sound level measured on a calibrated artificial ear when the hearing threshold of a subject is being measured with a standardized sound source.

It is a further object to provide means for improving the fidelity of the sound produced at the eardrum by an earphone assembly when said earphone assembly comprises a noise attenuating outer shell and cushion subassembly, within which an electroacoustic sound source provides an acoustic signal that is carried to the ear through an earpad assembly comprising a spring means that presses a resilient earpad cushion against the irregular contour of the pinna of the user's ear.

It is a further object to provide a simple means for approximating equal phase difference along the acoustic path from the source of sound to the ear, at any frequency within one or more ranges of frequencies of interest, in the audible frequency range, for two like noise excluding, earphone or earmuff, noise attenuating assemblies, of the type hereabove described, when worn as a pair.

Numerous other features, objects and advantages of the invention will now become apparent from the following specification when read in connection with the accompanying drawing in which:

DESCRIPTION OF THE PREFERRED EMBODIMENTS

Figure 1:
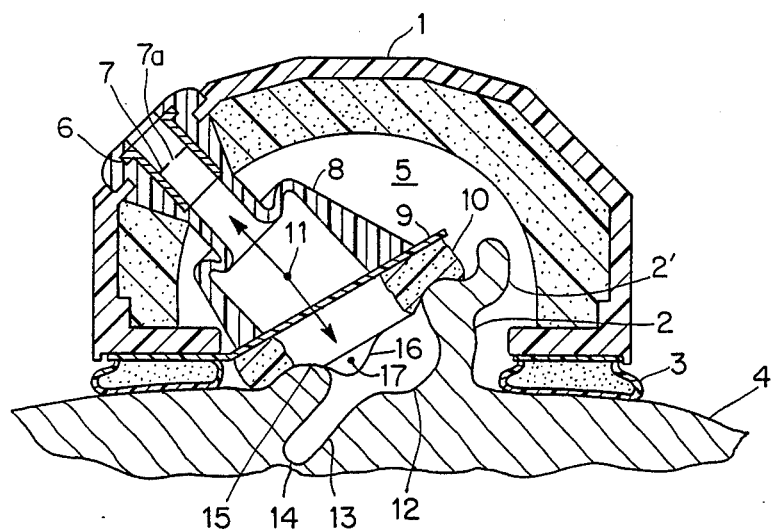
FIG. 1 is a cross section through a circumaural earmuff cup with a nonlinear bypass assembly.

Referring now to the drawings and more particularly FIG. 1, wherein there is shown a sectional view of a conventional earmuff cup assembly with a nonlinear bypass assembly according to some of the teachings of U.S. Pat. No. 4,441,576. The assembly is cut horizontally across its center as it is worn and viewed from below. A typical hard shell 1 covers the ear 2 and rests on a cushion 3 that presses against the head 4 to provide an acoustic seal, restricting the entrance of sound into the large cavity 5. Said shell has a nonlinear bypass comprising a cartridge 6 sealed into said shell and comprising an orifice plate 7 with at least one orifice 7a that admits sound from outside to pass through said cartridge thereby serving as a source of sound radiation into a passageway of small volume, referred to generally as 11, enclosed by an earpad assembly (comprising a duct 8, flange 9, and earpad cushion 10) and the concha 12, ear canal 13 and eardrum 14 of the user, said duct being acoustically sealed to said shell around said cartridge at one end and to said flange at the other end.

Whereas the external portion of the ear 2, comprising the pinna 2' and the tragus 15, has an irregular shape that differs widely from one person to another and generally has at least one valley 16, so deep and narrow that even a very soft and compliant earpad cushion 10 cannot conform to its contour without excessive pressure against the ear, there usually occurs some one (or more) leakage opening(s) 17 through which sound may communicate from the said passageway of small volume 11 to the large volume of cavity 5 inside the earcup shell 1, but outside the confines of passageway 11.

It has been found that the leakage opening 17 varies in size from one person to another and from one positioning to another on the same person, causing a large variation in the sound pressure level (SPL) measured at the eardrum. This variation is most readily shown as the measured insertion loss (IL) which is the decibel difference between the SPL at the eardrum with no protection and the SPL at the eardrum with the earmuff cup assembly properly positioned over the ear, both measured with the same incident sound field.

Figure 2:
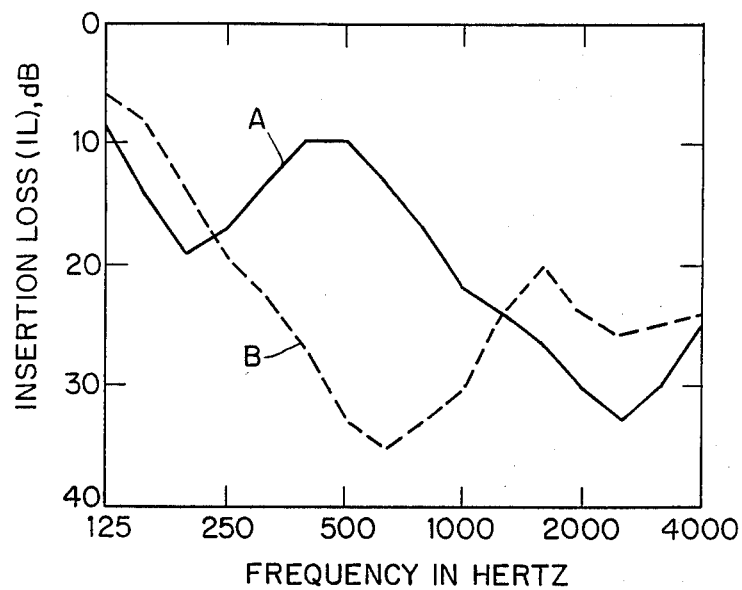
FIG. 2 is a graph showing values of insertion loss over a broad frequency range for the hearing protector of FIG. 1.

FIG. 2 shows a graph of such IL measurements made with a suitable acoustic test fixture (ATF), often referred to as an artificial head, with a microphone at the eardrum position. At frequencies near 500 Hz, a total variation exceeding 20 dB was observed between curve A measured with the earpad effectively sealed to the pinna (as sometimes occurs with a soft, relatively flat ear), here simulated using a soft moldable clay material, and curve B with a leakage opening 17, of approximately 1.2 cm$^2$ total open area, which is substantially equivalent to that occasionally found with a firm, sharply-contoured pinna.

Such variations are unacceptable for an HPD of the type described, wherein the sound level at the ear is intended to provide the clearest possible hearing for speech, warning signals and the like, while at the same time, providing a minimum, but reliably adequate protection against noise induced hearing loss.

Figure 3A:
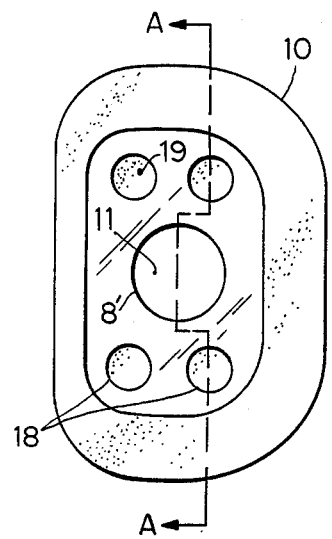
FIGS. 3a–3c show three views, some in section, of an earpad assembly comprising a preferred embodiment of the invention.
Figure 3B:
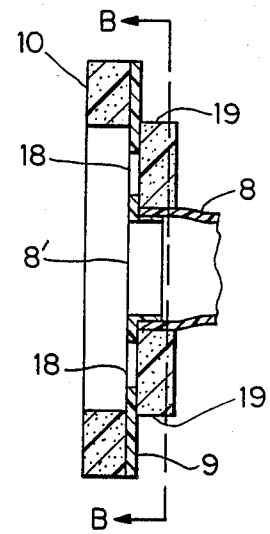
Figure 3C:
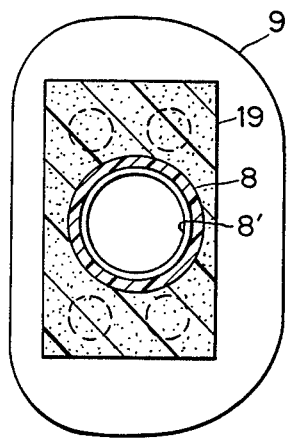

To reduce such variations, one or a plurality of acoustical leakage holes 18, as shown in FIG. 3, was cut through the flange 9 so that, even if the earpad cushion effectively seals against a soft relatively flat ear, there will always be a sizable leak. The total open area of the acoustic leakage path can be between 0.5 and 2 cm$^2$. When the total open area of said leakage holes 18 was approximately 1.25 cm$^2$, which was approximately equal to the open area of the largest leakage opening 17 commonly encountered between the surface of the earpad cushion 10 and the external surface of a real ear, the variation in IL was reduced to only a few dB, but the insertion loss spectrum closely resembled that of curve B in FIG. 2, which was far from the flat spectrum desired.

The high value of IL in the frequency range near 500 Hz was found to be due to an acoustic interaction between the small volume of the passageway 11 and the large volume of cavity 5 of FIG. 1. Said interaction was satisfactorily controlled by adhering a suitable layer of acoustical foam 19 to the back side of flange 9 so as to form a continuous bond around the edges of leakage holes 18.

Figure 4:
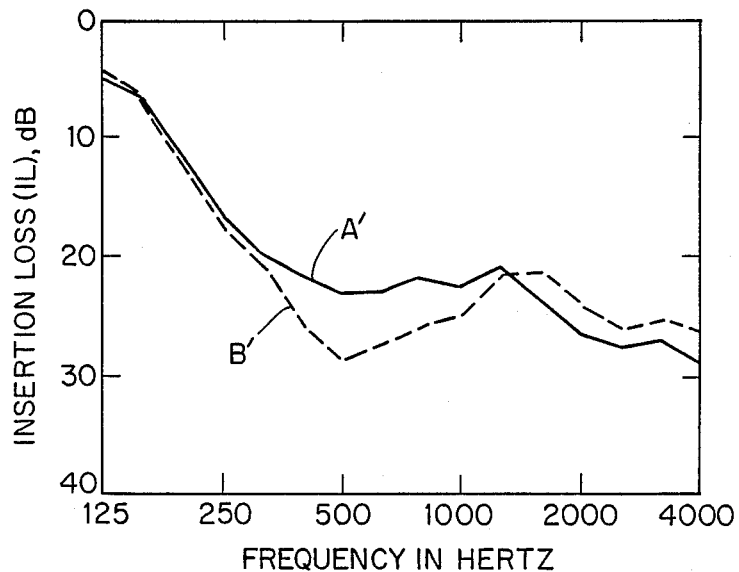
FIG. 4 is a graph similar to FIG. 2 but showing the benefit of the invention.

This change produced an IL spectrum that was flat and stable within ±4 dB over the frequency range of 400 to 4000 Hz, as shown in FIG. 4, where curve A' is the IL spectrum measured with the earpad sealed to the pinna of the ATF . using a soft clay-like material and curve B' is the similar spectrum measured with a leakage opening 17 equal to approximately 1.4 cm$^2$, somewhat larger than the largest commonly encountered with real ears. For these measurements, the leakage holes 18 had a total area of approximately 1.25 cm$^2$ and a total acoustic resistance with acoustically resistive material of between $3 \times 10^5$ and $4 \times 10^5$ SI acoustic ohms, N sec/m$^5$ (measured as the linear component of dc flow resistance, i.e., the value obtained from the measured values of flow resistance, over a range of flow speeds, regressed to the limiting value at zero flow speed).

It is to be understood that similar results can be obtained when the size and number of leakage openings 18 through the flange of the earpad are varied as may be convenient or necessary to adapt them to the geometry and materials of the earpad assembly, provided their effective total area and the acoustic resistance is maintained substantially constant.

It is further noted that the frequency of the predominant interaction, i.e., the resonance frequency, between the small volume of passage 11 and the larger volume of cavity 5 will depend upon the actual volumes of these two spaces and total open area of the openings 18. The magnitude of this resonance and its variation resulting from uncontrollable leakage between the earpad and the pinna can be controlled by the magnitude of the effective acoustic resistance supplied by the layer of acoustic foam 19 that is bonded to the back side of flange 9.

The invention comprising the use of prescribed acoustical leakage holes 18 through an earpad assembly ma be used in related applications where the sound from a confined source is fed through an earpad assembly in contact with the ear and where the resulting SPL at the ear is adversely influenced by uncontrollable acoustical leakage between the adjacent surfaces of the earpad cushion and the ear.

Figure 5A:
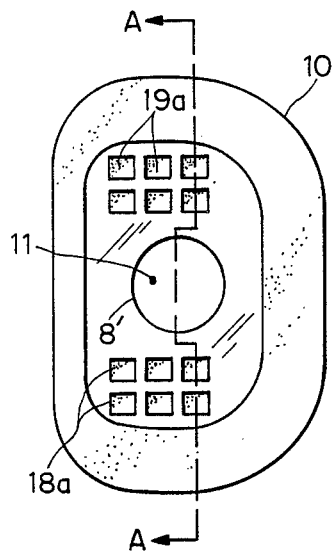
FIGS. 5a–5c show three views, some in section, of a second preferred embodiment of the invention.
Figure 5B:
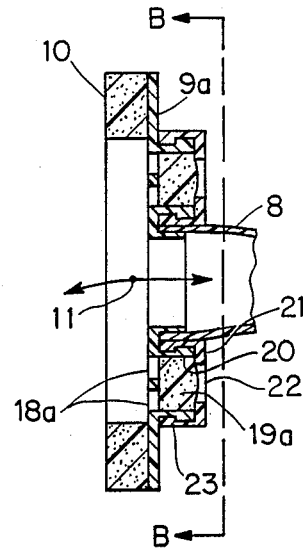
Figure 5C:
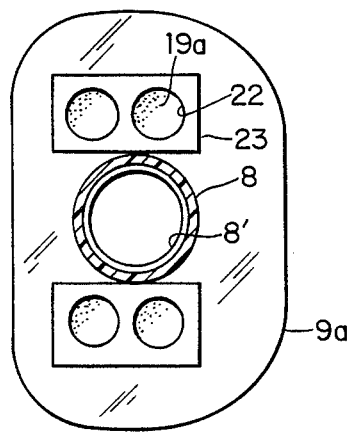
Figure 6A:
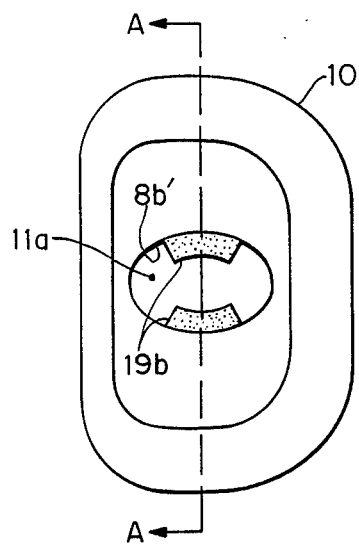
FIGS. 6a–6d show 4 views, some in section, of a third preferred embodiment of the invention.
Figure 6B:
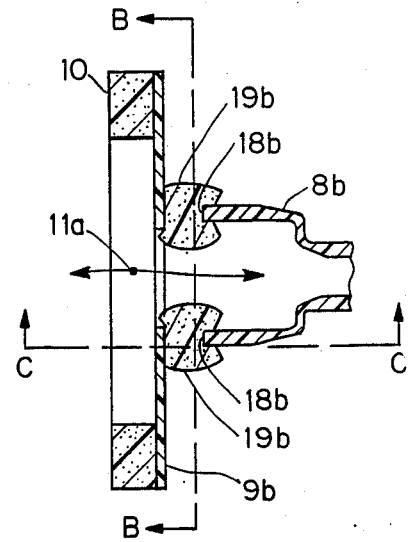
Figure 6C:
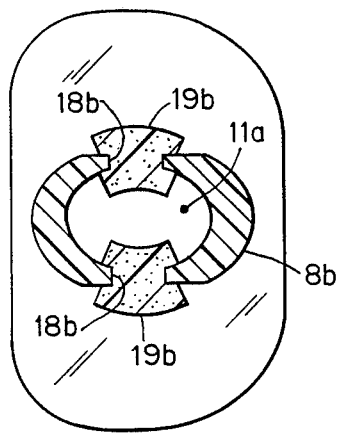
Figure 6D:
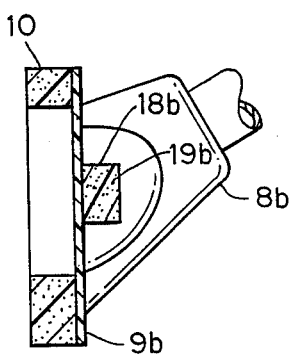

Referring now to FIGS. 5a–5c illustrating a second preferred embodiment of an earpad designed in accordance with the invention, a plurality of leakage holes 18a in two groups on opposite sides of the duct opening 8' penetrate through the flange 9a, which is molded with an open cup 20 on its back side surrounding each group of openings 18a, to receive a tightly fitting, piece of acoustically resistive material 19a such as felt or polyurethane foam designed to provide said prescribed acoustical resistance when locked into position by a snapfitting cap 21 having one or a plurality of openings 22 to form a cage (referred to generally as 23) for the resistive material, thereby confining the communicating sound to pass directly through the acoustical material without the need of any bonding or sealing material thus obtaining a reliable and repeatable acoustic resistance amenable to an automated production process.

Referring to FIGS. 6a–d illustrating another preferred embodiment of a duct and earpad assembly designed in accordance with the invention, the duct 8b is shown with two openings 18b in its side wall to allow sound communication between passage 11a and cavity 5, each opening 18b capturing within it a preshaped piece of acoustically resistive material 19b such as felt or polyurethane foam that is compressed against flange 9b as it is confined in said opening so as to assure its stable retention and to provide the prescribed value of total acoustic resistance necessary to control the spectral shape and uniformity of IL as herebefore described.

Figure 7:
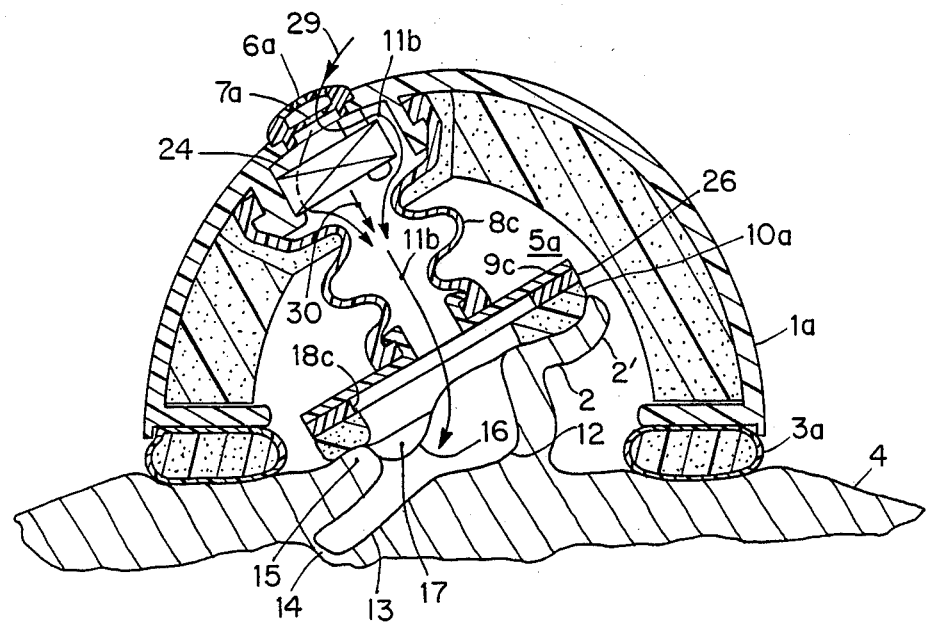
FIG. 7 is a cross section of a circumaural hearing protection device comprising two sound sources an orifice, and an earphone in yet another preferred embodiment of the invention.

Refer now to FIG. 7 illustrating an ear enclosure comprising a circumaural cushion 3a and a shell 1a that accommodates a cartridge 6a comprising an orifice 7a that admits a portion of the external incident sound 29 which forms a first source of sound, which passes to pass through the shell 1a of the enclosure and which radiates as an entering sound signal into a passageway of small volume 11b comprising one or a plurality of passages around an electroacoustic signaling device 24, acting as a second source of sound, said passages then converging into a common flexible duct 8c sealed to shell 1a at 31 around said electroacoustic signaling device, and sealed to flange 9c at 32, serving to carry sound 29 from the cartridge 6a and sound 30 from said electroacoustic signaling device 24 directly to the eardrum through an earpad cushion 10a pressed against the ear of the user by a small spring force provided either by said duct itself or by auxiliary spring means (not shown). The embodiment of the invention shown here comprises a layer of acoustical resistive material 26 inserted between the flange 9c and the earpad cushion 10a thereby forming at least one acoustic leakage hole 18c which, by proper choice of the structure, shape and size, of the resistive material 26 furnishes also the amount of total acoustic resistance required to control the interactive resonance between said passageway of small volume 11b and cavity 5a inside said shell 1a, but outside said passageway of small volume so as to stabilize the sound level at the eardrum and suitably control the shape of the IL between the sources of sound (2a and 24) and said eardrum.

Figure 8:
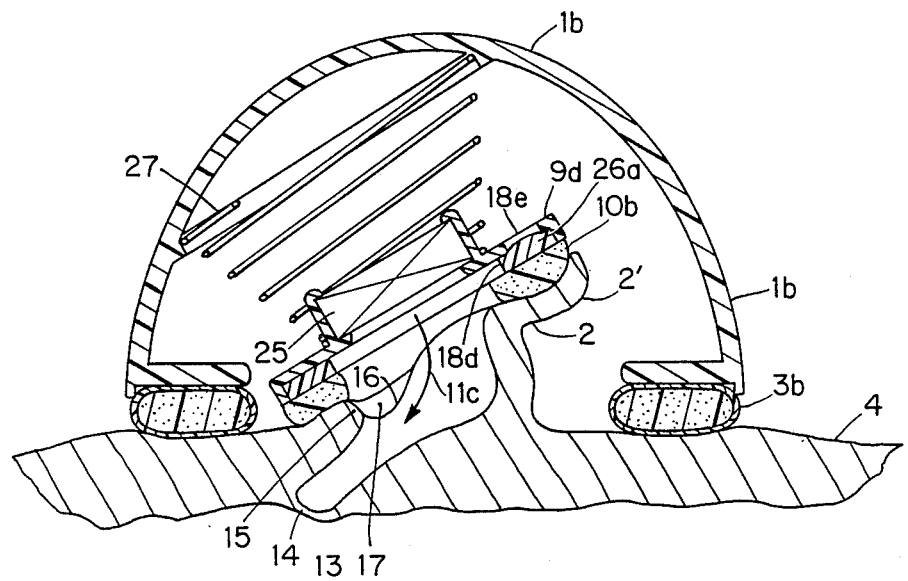
FIG. 8 is a cross section of a circumaural ear enclosure comprising an earphone assembly and another preferred embodiment of the invention.

Refer now to FIG. 8, in which there is shown a conventional ear enclosure comprising a rigid massive shell 1b supported on circumaural cushion 3b, enclosing an electroacoustic transducer, comprising the at least one source of sound, here referred to as an earphone 25, attached to an earpad assembly comprising a flange 9d, and an earpad cushion 10b, forming an acoustic passage of small volume 11c that carries at least some of the sound generated by said earphone directly to the eardrum of the user when the earpad cushion 10b is gently pressed against the external ear of the user by a spring means such as 27 acting between shell 1b and flange 9d. The invention comprises at least one opening 18d–e through the earpad assembly, in which is located a prescribed amount of acoustically resistive material 26a to control and reduce the variation in sound level at the eardrum that is otherwise created by uncontrollable sound leakage through opening 17 between the surface of said earpad cushion 10b and the surface of the external ear of the user.

What is claimed is:

1. In a sound attenuating ear enclosure comprising a circumaural cushion, resting against the head around the ear supporting a rigid, massive shell, within which there is at least one localized source of sound that radiates a sound into an acoustic path of small volume that conducts at least a portion of said sound directly to the eardrum of the user, wherein said acoustic path of small volume comprises a confining structure comprising an earpad assembly and the user's ear, wherein said earpad assembly comprises a duct, a flange and an earpad cushion, wherein said earpad cushion is lightly pressed against the user's ear by a force exerted through said earpad assembly:

the improvement comprising apparatus for reducing the variation in sound level at the eardrum of the user, said apparatus comprising at least one specifiable acoustic side branch circuit comprising an acoustic leakage path through said earpad assembly, to carry at least some sound from said acoustic path of small volume to a larger volume comprising the space confined between the inside surface of said ear enclosure and the outside surface of the said confining structure of said acoustic path of small volume, thereby maintaining said at least one specifiable leakage path as a minimum path for the purpose of reducing the variation in sound level at the eardrum that results from the uncontrollable, acoustic leakage openings between the adjacent surfaces of said earpad cushion and the external ear of the user, caused by the irregular size and shape of the external ear from one user to another and by the variation in the force of contact and the positioning of said earpad assembly upon the external ear of the user.

2. The improvement in accordance with claim 1 wherein said acoustic leakage path through said earpad assembly comprises at least one hole through said earpad assembly connecting said acoustic passage of small volume with said larger volume confined within said ear enclosure.

3. The improvement in accordance with claim 2 wherein the total open area of said acoustic leakage path is approximately equal to the total are of the largest uncontrollable leakage opening commonly encountered between said earpad cushion and said external ear of a user.

4. The improvement in accordance with claim 3 wherein the total open area of said acoustic leakage path is between 0.5 and 2 cm$^2$.

5. The improvement in accordance with claim 4 and further comprising acoustically resistive material in said acoustic leakage path.

6. The improvement in accordance with claim 5, wherein said acoustically resistive material provides a total acoustic resistance through said acoustic leakage path having a value between $3 \times 10^5$ and $4 \times 10^5$ SI ohms.

7. The improvement in accordance with claim 5 wherein the value of said total acoustic resistance is between $1 \times 10^5$ and $10 \times 10^5$ SI ohms.

8. The improvement in accordance with claim 1 wherein said sound attenuating ear enclosure is a hearing protection device.

9. The improvement in accordance with claim 1 wherein said sound attenuating enclosure is a hearing protection device and wherein said at least one localized source of sound is an electroacoustic transducer that is part of an active means for altering the effective sound reduction or attenuation of said enclosure.

10. The improvement in accordance with claim 1 wherein said ear enclosure is a hearing protection device and wherein said at least one localized source of sound comprises a portion of the incident external sound which radiates as an entering sound signal into said acoustic path of small volume through an orifice in said rigid massive shell, wherein the acoustic path of small volume comprises at least one passage passing around an acoustic transducer and entering the confining structure comprising an earpad assembly and the user's ear, wherein further, said earpad assembly comprises a duct sealed at one end to said rigid massive shell around said transducer, such that, the sound signal generated by said transducer radiates directly into said duct and combines with said entering sound signal such that at least a portion of both signals passes through said earpad assembly directly to the eardrum of the user.

11. The improvement in accordance with claim 1 wherein said ear enclosure comprises said circumaural cushion supporting said rigid massive shell and said at least one source of sound comprises an earphone that is acoustically sealed to and radiates sound into said passageway of small volume comprising said earpad assembly pressed against the external ear of the user by spring means.

* * * * *